United States Patent [19]

Angelchik

[11] 4,271,827
[45] Jun. 9, 1981

[54] METHOD FOR PREVENTION OF GASTRO ESOPHAGEAL REFLUX

[76] Inventor: Jean P. Angelchik, 1728 W. Glendale Ave., Suite 401, Phoenix, Ariz. 85021

[21] Appl. No.: 75,270

[22] Filed: Sep. 13, 1979

[51] Int. Cl.³ .......................... A61B 19/00; A61F 1/00
[52] U.S. Cl. ..................................................... 128/1 R
[58] Field of Search .................. 3/1; 128/1 R, 334 R, 128/325, 95, 346, 96, DIG. 23, DIG. 25

[56] References Cited

U.S. PATENT DOCUMENTS 3,875,928  4/1975  Angelchik ........................... 128/1 R Primary Examiner—Frank A. Spear, Jr.
Attorney, Agent, or Firm—Drummond and Nelson

[57] ABSTRACT

A method for preventing gastro esophageal reflux when the gastro esophageal junction is positioned above the diaphragm. The method comprises positioning a generally C-shaped cushion prosthesis about the distal esophagus, adjusting the free ends of the prosthesis at a spacing to permit normal expansion of the esophagus during swallowing and fixing the free ends of the prosthesis in the adjusted position to maintain the prosthesis in operative position around the distal esophagus adjacent to the gastric fundus when the gastro esophageal junction is positioned above the diaphragm and to maintain the adjusted spacing of the free ends. The inside diameter of the prosthesis generally corresponds to the normal outside diameter of the distal esophagus, and the C-shaped member is deformable to permit adjustment of the spacing of the free ends at a selected distance.

1 Claim, 6 Drawing Figures

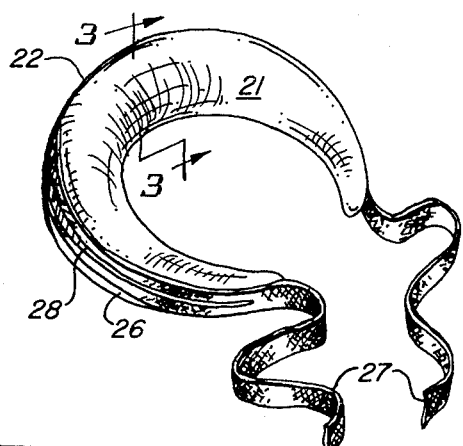
FIG_2
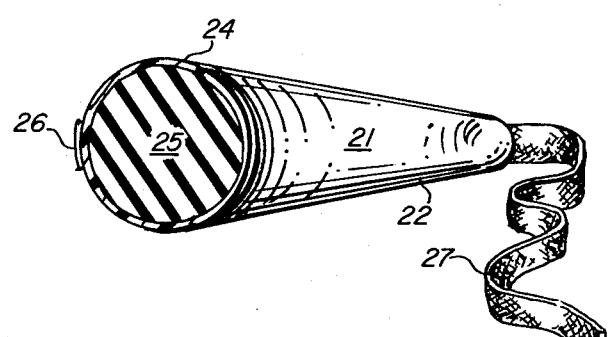
FIG_3
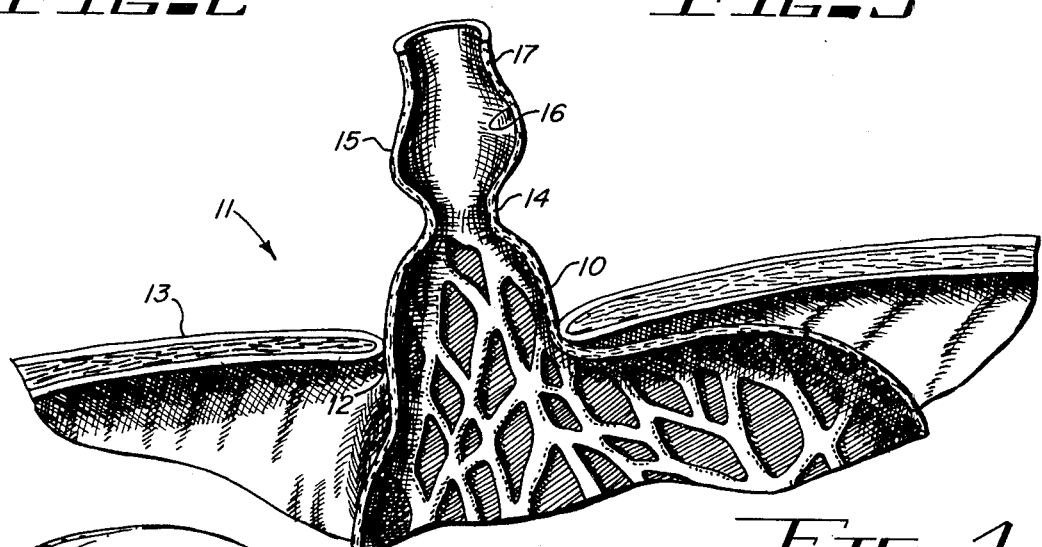
FIG_1
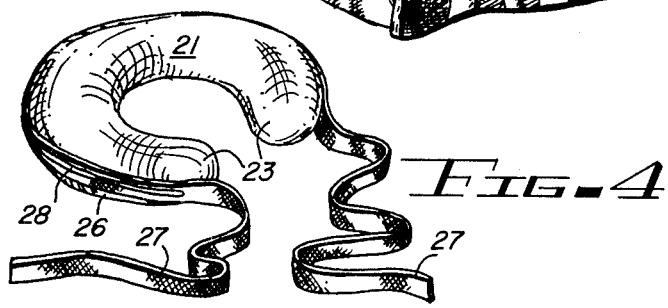
FIG_4
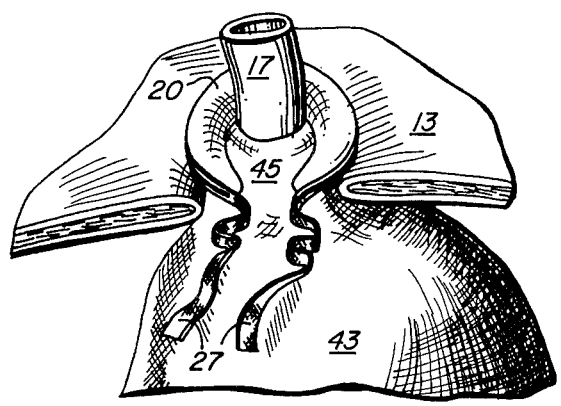
FIG_5
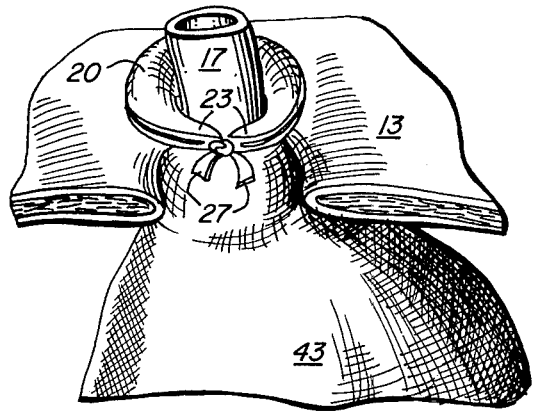
FIG_6

METHOD FOR PREVENTION OF GASTRO ESOPHAGEAL REFLUX

This invention relates to methods for using a surgical prosthesis.

More particularly, the invention concerns an improved method for using a surgical prosthesis to prevent gastro esophageal reflux.

When the esophageal hiatus of the diaphragm muscle becomes enlarged, a portion of the stomach immediately below the gastro esophageal junction (the gastric fundus) may actually slide upwardly through the esophageal hiatus into the chest or thoracic cavity. This anatomic condition, known as a "sliding esophageal hernia" frequently causes gastro esophageal reflux in which stomach acids and foods are regurgitated into the esophagus. The characteristic symptoms of gastro esophageal reflux consist of substernal burning, regurgitation and frequent eructations. These symptoms are accentuated by recumbency, tight garments and physical activity, particularly bending at the waist. Long-term gastro esophageal reflux leads to complications, namely dysphagia from an esophageal stricture.

Various procedures have been devised for the repair of sliding esophageal hernias and for the prevention of gastro regurgitation and eructations. Crural repair almost invariably fails since it is almost impossible to effectively suture the constantly moving diaphragm. Therefore, other procedures to prevent the stomach from sliding through the enlarged esophageal hiatus were devised. According to the "posterior gastropexy" procedure of Hill, the crura is closed behind the esophagus and the stomach is sutured to the arcuate ligament over the aorta to hold the stomach within the abdominal cavity. According to the "Niessen II" procedure, the gastric fundus is formed into a ring around the distal esophagus. The added bulk of this ring around the esophagus forms a valve preventing regurgitation and, at the same time, preventing the stomach from sliding through the enlarged esophageal hiatus.

The Hill procedure described above is very difficult to perform on obese patients and it appears that the sutures from the lesser curvature of the stomach to the arcuate ligament are of a transient nature. According to the Niessen II procedure, it is necessary to suture the stomach to itself and to the esophagus.

My earlier issued U.S. Pat. No. 3,875,928 discloses a further method for maintaining the reduction of a sliding esophageal hiatal hernia. The method comprises emplacing a C-shaped prosthesis about the distal esophagus between the gastric fundus and the diaphragm. The prosthesis has a tape secured about the periphery thereof. The free ends of the tape, which extend well beyond the tapered ends of the C-shaped cushion, are tied together then sutured to the stomach to maintain the prosthesis in proper operative position.

As evidenced by the Hill and Niessen II procedures described above and by the method described in my earlier issued U.S. Pat. No. 3,875,928, it is a common practice to attempt to maintain the stomach in its natural position below the diaphragm in order to prevent gastro esophageal reflux.

However, according to the procedure which I have devised, utilizing the prosthetic device described herein, it is unnecessary to maintain the stomach below the diaphragm by reducing the esophageal hiatus or by suturing the stomach to itself or to any other anatomical structure. In fact, my improved procedure requires no suturing whatsoever.

Accordingly, it is a principle object of the present invention to provide an improved method for preventing gastro esophageal reflux.

Another object of the invention is to provide an improved method for preventing gastro esophageal reflux when the gastro esophageal junction is positioned above the diaphragm.

Still another object of the invention is to provide an improved method for preventing gastro esophageal reflux which does not require suturing or require reduction of the esophageal hiatus.

Yet another object of the invention is to provide an improved method for preventing gastro esophageal reflux in which a prosthesis acts as a mechanical valve to prevent gastro esophageal reflux.

These and other further and more specific objects and advantages of the invention will be apparent to those skilled in the art from the following detailed description thereof, taken in conjunction with the drawings, in which:

FIG. 1 is a cross sectional view of the stomach, diaphragm and esophagus illustrating a typical sliding esophageal hernia;

FIG. 2 is a perspective view of the prosthesis which I use in accordance with the preferred embodiment of my improved procedure for preventing gastro esophageal reflux;

FIG. 3 is a sectional perspective view of the prosthesis of FIG. 2 taken at section line 3—3 thereof;

FIG. 4 is a perspective view of a prosthesis which may optionally be used in accordance with the preferred embodiment of my improved procedure for preventing gastro esophageal reflux;

FIG. 5 is a perspective anatomical drawing illustrating the initial steps in the implantation of the prosthesis of FIGS. 2-3; and FIG. 6 is a perspective anatomical drawing illustrating the prosthesis of FIGS. 2-3 located in its proper operative position to prevent gastro esophageal reflux.

Briefly, in accordance with my invention, I provide an improved method for preventing gastro esophageal reflux when the gastro esophageal junction is positioned above the diaphragm. The method comprises positioning a generally C-shaped cushion prosthesis around the distal esophagus, adjusting the free ends of the prosthesis at a spacing to permit normal expansion of the esophagus during swallowing, and fixing the free ends of the prosthesis in the adjusted position to maintain the C-shaped cushion prosthesis in operative position around the distal esophagus generally adjacent to the gastric fundus when the gastro esophageal junction is positioned above the diaphragm and to maintain the adjusted spacing of free ends. The C-shaped cushion has an inside diameter generally corresponding to the normal outside diameter of the distal esophagus, and is deformable to permit adjustment of the spacing of the free ends thereof at a selected distance.

The prosthesis employed in my improved method bears radiopaque indicia which facilitate radiographic determination of the position of the prosthesis after emplacement thereof around the distal esophagus. The means for maintaining the cushion member in its operative position preferably comprises an elongate tape member secured around the periphery of the cushion member. The free ends of the tape extend substantially beyond the free ends of the C-shaped cushion member, i.e., a distance sufficient to allow the ends of the tape member to be tied together.

Turning now to the drawings, FIG. 1 depicts a typical sliding esophageal hiatal hernia and shows the gastric fundus 10 extending into the thoracic cavity 11 through the enlarged esophageal hiatus 12 of the diaphragm 13. In this position, the lesser sphincter 14 of the esophagus 15, being transposed into the chest from its normal position just below the esophageal hiatus 12 operates less effectively. This permits gastro esophageal reflux of stomach acids and foods which are not evacuated by esophageal peristalsis and which remain in the lower esophagus for prolonged periods causing irritation and damage to the lower esophagus mucosa 16.

FIG. 2 depicts the prosthesis device which I utilize in the preferred embodiment of my improved method for preventing gastro esophageal reflux. The prosthesis consists of a generally C-shaped cushion member 21, the inside dimensions of which generally correspond to the normal outside dimensions of the distal esophagus (reference character 17, FIG. 5). In a typical prosthesis, the inside dimensions will equal about 3.75 by 2.5 centimeters and the outside dimensions will equal about 6.25 by 5.25 centimeters, although prosthetic devices having somewhat larger and somewhat smaller inner and outer dimensions should be provided to the surgeon for use where the patient may have an esophagus somewhat larger or somewhat smaller than normal.

In accordance with the prosthesis as shown in FIGS. 2-3, the cushion member has a generally circular cross-section and is tapered from the central portion 22 toward the free ends thereof 23. The prosthesis is preferably constructed by filling outer flexible integement 24 with a gel liquid 25 such that the entire cushion member 21 is deformable to permit adjustment of the spacing of the free ends 23 at a selected distance which will permit the normal expansion of the esophagus during swallowing. The precise materials of construction of the integement 24 and the filler 25 of the C-shaped cushion member 21 are not highly critical so long as they are compatible with body tissues, i.e., do not induce rejection or cause other body reaction. In the presently preferred prosthesis, I employ a silicone elastomer shell filled with a highly cross linked silicone gel. A tape 26, preferably silicone-coated Dacron, is secured to the C-shaped cushion member 21 around the outer periphery thereof and the free ends 27 of the tape extend substantially beyond the free ends 23 of the C-shaped cushion member 21 to a distance sufficient to allow the free ends 27 of the tape 26 to be tied together.

Preferably, the prosthesis is provided with a tantalum filled silicone strip 28 on tape 26 such that after implantation of the prosthesis, radiographic examination will reveal whether the prosthesis is in its proper operative position.

A prosthesis which may optionally be employed in my improved method is illustrated in FIG. 4. The prosthesis is of generally constant cross-sectional area along its entire length, i.e., the ends of the prosthesis are not substantially tapered. In a typical prosthesis of this shape and contour, the inside dimensions will equal about 3.1 by 2.5 centimeters and the outside dimensions will equal about 6.0 by 7.0 centimeters. Obviously, a variety of variously sized and shaped prosthetic devices could be employed in my improved method for preventing gastro esophageal reflux.

The method of use of the prosthesis of FIGS. 2-3 is illustrated in FIGS. 5 and 6. My procedure consists of opening the abdominal cavity with an upper midline incision and exposing the area of the diaphragmatic hiatus. As shown in FIG. 5, the prosthesis 20 of FIGS. 2-3 is then placed around the distal esophagus 17 immediately above the gastric fundus 45. FIG. 6 illustrates the prosthesis 20 in position after the free ends 27 of the tape 26 are anteriorly tied at 46 to locate the free ends 23 of the prosthesis 20 at the proper spacing and after the tape end remnants are cut leaving about an inch of length. The prosthesis 20, when emplaced around the distal esophagus immediately above the stomach, acts as a mechanical valve and generally precludes regurgitation while permitting the regular downward flow of food from the esophagus to the stomach.

Intra abdominal retraction of the stomach 43 through the esophageal hiatus 12 prior to emplacement of the prosthesis 20 is not required. Similarly, reduction of or suturing of the diaphragmatic hiatus 12 is not necessary before or after the prosthesis 20 is in operative position.

In order to prevent gastro esophageal reflux, the method described in my earlier issued U.S. Pat. No. 3,875,928 attempts to preclude upward migration of the stomach through the esophageal hiatus by suturing a prosthesis emplaced around the esophagus to the stomach. As described herein, my improved method, without any suturing whatsoever and without reduction of the hiatal hernia, prevents gastro esophageal reflux by placing a prosthesis around the esophagus when the gastro esophageal junction is located above the diaphragmatic hiatus.

Having now described my invention and the use thereof in such clear, concise and exact terms as to enable those skilled in the art to understand the invention and practice it, and having identified the presently preferred embodiments of the invention, I claim:

1. A method for preventing gastro esophageal reflux when the gastro esophageal junction is positioned above the diaphragm, said method comprising:
   (a) positioning a generally C-shaped cushion prosthesis around the distal esophagus, the inside diameter of said prosthesis generally corresponding to the normal outside diameter of the distal esophagus, said C-shaped member being deformable to permit adjustment of the spacing of the free ends thereof at a selected distance;
   (b) adjusting said free ends of said prosthesis at a spacing to permit normal expansion of the esophagus during swallowing; and
   (c) fixing said free ends of said prosthesis in said adjusted position to maintain said C-shaped cushion prosthesis in operative position around the distal esophagus generally adjacent to the gastric fundus when the gastro esophageal junction is positioned above said diaphragm and to maintain said adjusted spacing of said free ends, said prosthesis being positioned above said diaphragm free of any sutures interconnecting said prosthesis with the human body.

* * * * *